(12) United States Patent
Wu

(10) Patent No.: US 10,220,221 B2
(45) Date of Patent: Mar. 5, 2019

(54) DENTAL DEVICE AND PHOTODYNAMIC THERAPEUTIC SYSTEM USING SAME

(71) Applicant: Olighter Co. Ltd., Tainan (TW)

(72) Inventor: Ping-Ching Wu, Tainan (TW)

(73) Assignee: Olighter Co., Ltd., Tainan (TW)

( * ) Notice: Subject to any disclaimer, the term of this patent is extended or adjusted under 35 U.S.C. 154(b) by 118 days.

(21) Appl. No.: 15/391,852

(22) Filed: Dec. 28, 2016

(65) Prior Publication Data

US 2018/0178031 A1 Jun. 28, 2018

(51) Int. Cl.
*A61C 1/00* (2006.01)
*A61N 5/06* (2006.01)
*A61C 19/06* (2006.01)
*A61L 2/00* (2006.01)
*A61N 5/067* (2006.01)

(52) U.S. Cl.
CPC .......... *A61N 5/0603* (2013.01); *A61C 19/063* (2013.01); *A61L 2/00* (2013.01); *A61N 5/062* (2013.01); *A61N 5/0624* (2013.01); *A61N 2005/063* (2013.01); *A61N 2005/0606* (2013.01); *A61N 2005/067* (2013.01); *A61N 2005/0651* (2013.01); *A61N 2005/0659* (2013.01); *A61N 2005/0661* (2013.01); *A61N 2005/0662* (2013.01)

(58) Field of Classification Search
CPC .... A61C 5/90; A61C 19/063; A61K 41/0057; A61N 5/0603; A61N 5/062; A61N 5/0624; A61N 5/1014; A61N 2005/0606; A61N 2005/063; A61N 2005/0651; A61N 2005/0661; A61N 2005/0662; A61N 2005/067; A61N 2005/1098
USPC .......................................................... 433/29
See application file for complete search history.

(56) References Cited

U.S. PATENT DOCUMENTS

| | | | | |
|---|---|---|---|---|
| 4,852,549 A * | 8/1989 | Mori | .................. | A61N 5/06 607/92 |
| 5,316,473 A * | 5/1994 | Hare | .................. | A61C 19/004 433/215 |
| 5,487,662 A * | 1/1996 | Kipke | .................. | A61C 9/0006 433/215 |
| 6,077,073 A * | 6/2000 | Jacob | .................. | A61C 19/066 433/29 |
| 6,368,109 B2 * | 4/2002 | Lindquist | .......... | A61C 9/0006 433/215 |
| 6,394,802 B1 * | 5/2002 | Hahn | .................. | A61C 9/0006 433/37 |
| 6,514,075 B1 * | 2/2003 | Jacob | .................. | A61C 1/088 433/29 |

(Continued)

*Primary Examiner* — Nicholas Lucchesi

(57) ABSTRACT

A dental device for treating dental infection includes a dental cast comprising at least one groove to receive teeth and/or gums of a dental arch of the patient; and at least one light diffusing fiber arranged on the dental cast around the at least one groove. The dental device is used in a photodynamic therapeutic system, in which a light source instrument emits light onto a photosensitizer applied in mouth of the patient. The dental device is optically coupled to the light source instrument. The light for treating dental infection of the patient is transmitted by the at least one light diffusing fiber of the dental device and activates the photosensitizer to produce free radicals or oxidants to destroy the bacteria and microbes causing dental disease.

21 Claims, 8 Drawing Sheets

(56) References Cited

U.S. PATENT DOCUMENTS

| | | | | |
|---|---|---|---|---|
| 6,616,447 B1* | 9/2003 | Rizoiu | A61C 19/063 | 433/216 |
| 6,893,259 B1* | 5/2005 | Reizenson | A61C 17/0211 | 433/29 |
| 6,976,841 B1* | 12/2005 | Osterwalder | A61C 9/0006 | 433/29 |
| 8,029,278 B1* | 10/2011 | Levine | A61C 19/066 | 433/215 |
| 9,211,420 B2* | 12/2015 | Patel | A61K 8/0208 | |
| 9,700,735 B2* | 7/2017 | Dabney | A61N 5/062 | |
| 9,726,435 B2* | 8/2017 | Dahm | A61C 19/004 | |
| 9,884,203 B2* | 2/2018 | Dabney | A61N 5/062 | |
| 9,974,630 B2* | 5/2018 | Heacock | A61C 7/08 | |
| 2004/0110111 A1* | 6/2004 | Wasylucha | A61C 19/063 | 433/29 |
| 2005/0064371 A1* | 3/2005 | Soukos | A61C 19/06 | 433/217.1 |
| 2005/0095553 A1* | 5/2005 | Gittleman | A61C 9/0006 | 433/37 |
| 2005/0202363 A1* | 9/2005 | Osterwalder | A61C 9/0006 | 433/29 |
| 2005/0266370 A1* | 12/2005 | Suzuki | A61C 19/063 | 433/29 |
| 2008/0096156 A1* | 4/2008 | Rose | A61C 1/0015 | 433/29 |
| 2008/0255498 A1* | 10/2008 | Houle | A61C 17/02 | 604/20 |
| 2011/0091835 A1* | 4/2011 | Levine | A61C 19/063 | 433/29 |
| 2011/0104633 A1* | 5/2011 | Levine | A61C 19/063 | 433/29 |
| 2012/0064477 A1* | 3/2012 | Schmitt | A61C 9/0006 | 433/29 |
| 2012/0183919 A1* | 7/2012 | Levine | A61C 19/063 | 433/29 |
| 2014/0072932 A1* | 3/2014 | Brawn | A61C 19/06 | 433/173 |
| 2014/0272770 A1* | 9/2014 | Hurley | A61C 19/063 | 433/29 |
| 2015/0072302 A1* | 3/2015 | Jablow | A61K 8/27 | 433/29 |
| 2015/0164618 A1* | 6/2015 | Heacock | A61C 7/08 | 433/6 |
| 2016/0015494 A1* | 1/2016 | Dabney | A61C 19/063 | 433/29 |
| 2016/0113747 A1* | 4/2016 | Almutairi | A61C 17/0211 | 433/27 |

* cited by examiner

DENTAL DEVICE AND PHOTODYNAMIC THERAPEUTIC SYSTEM USING SAME

FIELD

The subject matter herein generally relates to a dental device and a photodynamic therapeutic system.

BACKGROUND OF THE INVENTION

The disinfection of pathogenic microbes in oral cavity is a means to treat dental infection. Generally, the dental infection includes periapical abscess, pericoronitis, periodontal abscess, periodontitis, pulpitis and caries, and may include the infection syndromes of oral and maxillofacial area.

The treatment of dental infection can use physical methods to scrape off tartar, plaque, and lesions, and/or use antibiotics or sodium hypochlorite aqueous to inhibit pathogenic microbes. However, the methods require a long course of treatment, causing damage to the normal gum tissue, and may have bacterial drug-resistance. Therefore, a safe and convenient method should be developed.

The present disclosure is described in relation to a photodynamic therapy (PDT) method. The PDT is a novel method for treating the dental infection. Bacteria accumulated in tooth surface, periodontal capsular, or dental pulp can be disinfected via the activated photosensitizers by a light illumination of the PDT. The PDT method shows several advantages. For example, the PDT method can disinfect the bacteria completely and reduce the treatment time by full oral cavity illumination. The method can disinfect against Gram positive bacteria, *Porphyromonas gumis*, or methicillin-resistant *Staphylococcus aureus*, and decrease the injury of alveolar bone by endotoxin from Gram negative bacteria. In addition, the PDT method can increase the success rate of treatment and reduce health care costs.

Features and advantages of the subject matter hereof will become more apparent in light of the following detailed descriptions of exemplary embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive in relation to the full scope of the subject matter as set forth in the claims.

BRIEF DESCRIPTION OF THE DRAWINGS

Implementations of the present technology will now be described, by way of example only, with reference to the attached figures.

DETAILED DESCRIPTION

Figure 1:
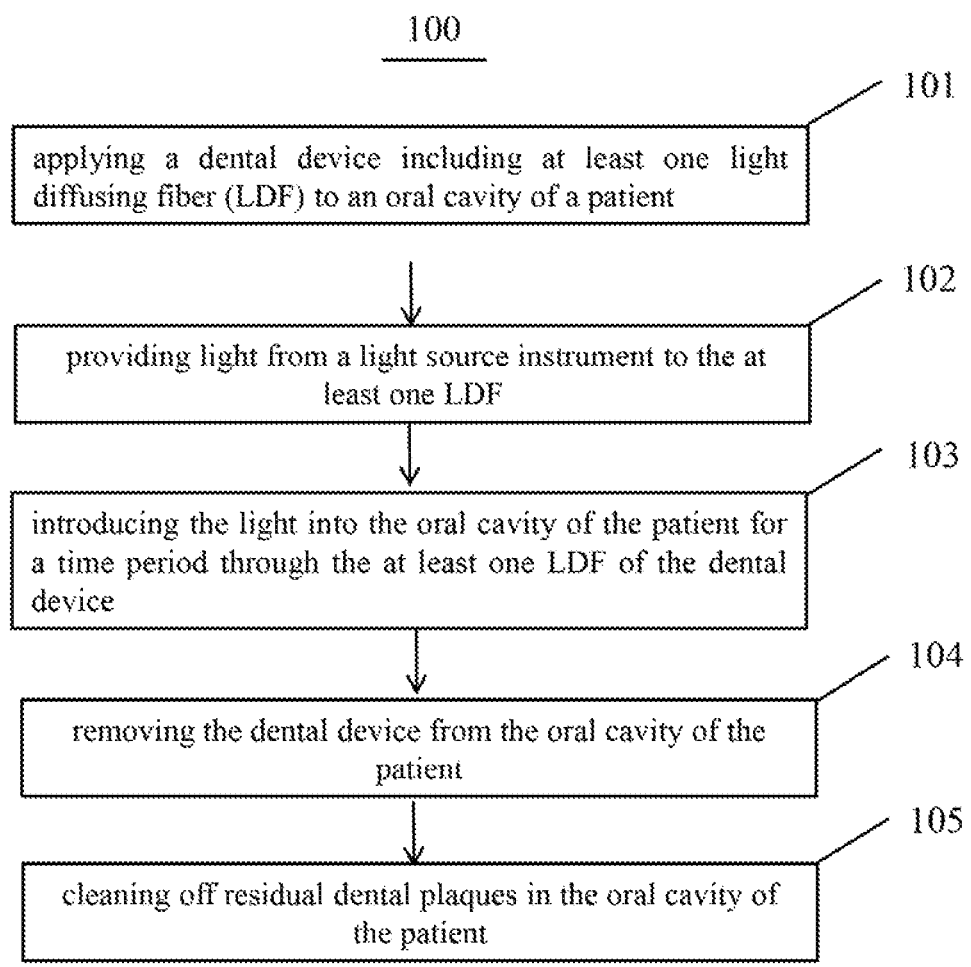
FIG. 1 is a block diagram of one exemplary embodiment of a photodynamic therapeutic method for treating dental infection.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "substantially" means essentially conforming to the particular dimension, shape or other feature that the term modifies, such that the component need not be exact. For example, "substantially cylindrical" means that the object resembles a cylinder, but may have one or more deviations from a true cylinder. The term "coupled" means connected, whether directly or indirectly through intervening components, and is not necessarily limited to physical connections. The connection may be such that the objects are permanently connected or releasably connected. The term "connecting" is defined as linked, whether directly or indirectly through intervening components, and is not necessarily limited to physical linking. The connection can be such that the objects are permanently connected or releasably connected. The term "comprising" or "containing" when utilized, means "including, but not necessarily limited to"; it specifically indicates open-ended inclusion or membership in the so-described combination, group, series and the like. The term "administering" means the dispensing of a therapeutic agent to treat a condition, which is given orally, intravenously, added to a "drip", subcutaneously, intramuscularly, or painted on the skin or mucosal. The term "applying" is the act of bringing things into contact or of starting an action. The term "irradiating" is the process by which an object is exposed to light or radiation. The term "illumination" is the lighting up of a part, cavity, organ, or object. The term "introducing" is intended to mean moving something (for example, light) from a specific resting position into a destination position along a planned direction.

The term "photosensitizer" is intended to mean a chemical compound capable of absorbing photons of an actinic light. The photosensitizer readily undergoes photo-excitation and transfers its energy to other molecules, thus enhancing or accelerating the dispersion of light, and enhancing or activating oxidant present in the reaction mixture is thus activated or enhanced. The term "oxidant" is a substance that has the ability to oxidize other substances or transfer oxygen atoms to other compounds, or a substance that gains electrons in a redox chemical reaction. The term "dye" is any of various colored substances containing auxochromes and thus capable of coloring substances to which they are applied. Dyes are used for staining and coloring, as test reagents, and as therapeutic agents. The term "dosage form" is a pharmaceutical drug in the form in which it is marketed for use in a particular configuration with a specific mixture of active ingredients and excipients, and pre-apportioned into a particular dose. The term "dental" is related to the study, diagnosis, prevention, and treatment of diseases, disorders and conditions of the oral cavity, commonly in the dentition but also the oral mucosa, and of adjacent and related structures and tissues.

The terms "first", "second", "third" and other terms in the present disclosure are only used as textual symbols as the circumstances may require, but such a practice of ordination is not limited to using only these terms. It should be further noted that these terms can be used interchangeably.

The present disclosure is described in relation to a dental device and a photodynamic therapeutic system for treating dental infection of a patient.

In one example, a dental device is disclosed. The dental device is for treating dental infection of a patient and includes a dental cast having at least one groove for receiving teeth and/or gums of a dental arch of the patient, and at least one light diffusing fiber arranged on the dental cast around the at least one groove. The at least one light diffusing fiber is configured to convey light treating dental infection of the patient.

In another example, a photodynamic therapeutic system is disclosed. The photodynamic therapeutic system treats dental infection of a patient and includes a dental device, a light source instrument emitting light, and a photosensitizer spread or sprayed to an oral cavity of the patient. The dental device includes a dental cast having at least one groove for receiving teeth and/or gums of a dental arch of the patient. The at least one light diffusing fiber is arranged on the dental cast around the at least one groove. The dental device is optically coupled to the light source instrument, the light is transmitted by the at least one first light diffusing fiber of the dental device to the oral cavity of the patient, and the photosensitizer is activated to produce free radicals or oxidants for treating dental infection of the patient.

Another example of the disclosure is a photodynamic therapeutic system for treating dental infection of a patient which includes a dental device and a light source instrument emitting light. The dental device includes a dental cast having at least one groove for receiving teeth and/or gums of a dental arch of the patient, and at least one light diffusing fiber arranged on the dental cast around the at least one groove. The dental device is optically coupled to the light source instrument, the light for treating dental infection of the patient is transmitted by the at least one light diffusing fiber of the dental device into an oral cavity of the patient.

As shown in FIG. 1, in the first embodiment, photodynamic therapeutic method for treating dental infection includes the following steps:

in block 101, applying a dental device including at least one LDF to an oral cavity of a patient;
in block 102, providing light from a light source instrument to the at least one LDF;
in block 103, introducing the light into the oral cavity of the patient for a time period through the at least one LDF of the dental device;
in block 104, removing the dental device from the oral cavity of the patient; and
in block 105, cleaning off residual dental plaques in the oral cavity of the patient.

The oral cavity of the patient can include a dental arch, tongue, maxilla, mandible and lips with muscle or soft tissue. The dental arch includes an upper dental arch and a lower dental arch. The upper dental arch and the lower dental arch include opposite raised molars. The upper dental arch and the lower dental arch of the dental arch include teeth and gums, and each tooth includes a dental crown, a cervix dentis, and a radices dentis. The soft tissue includes a gum surrounding and covering each tooth. An alveolar process defines a portion surrounded by the maxilla and the mandible, and supported by the radices dentis. The gum includes gingiva defined an oral mucosa covering between the cervix dentis and a surface of the alveolar process. The lips include an upper lip and a lower lip.

The dental infection may include, but is not limited to, periapical abscess, pericoronitis, periodontal abscess, periodontitis, pulpitis, gingivitis, and caries. The dental infection may include other oral or maxillofacial infection. The most common form of gingivitis is a reaction to bacterial biofilm attached to tooth surfaces. The caries is a breakdown of teeth due to activities of bacteria.

The dental device may be constructed as a dental brace. In one example, the dental brace may be based on a dental bite. The dental brace includes a dental cast arranging the at least one LDF and a connector optically coupled to the at least one LDF. Each LDF may be detachably fitted on the dental cast. The at least one LDF may be detachably and optically coupled to the connector. The at least one LDF is configured to introduce/transmit the light to the gums, the teeth, the tongue, and/or the soft tissue of lips of the patient. An exterior of the dental cast may be substantially a U shape, a horse-shoe shape, or a slice to attach to the teeth or gums of the patient. The dental cast may be formed from any material that is biocompatible. For example, the material of the dental cast may be selected from the group consisting of a polymethylmethacrylate, polyethylene, polycarbonate, polyvinylchloride, polypropylene, polydimethylsiloxane, polytetrafluoroethylene, polyurethane, rubberized polymer, or any combination thereof. In one embodiment, the dental cast may include an upper alveolar and a lower alveolar. The upper alveolar and the lower alveolar each include a positioning slot for setting an LDF. In another embodiment, the dental cast may only include an upper alveolar or a lower alveolar with a positioning slot for setting the LDF. The alveolar is any container shaped for the embedding of teeth and/or gums of the patient. The alveolar may be at least partially made of a flexible material and at least partially made of a stiff material configured to support components of the dental device.

The dental cast includes at least one groove for receiving the dental arch of the patient, and the at least one LDF is arranged on the dental cast around the at least one groove. The at least one groove has two ends. One end of the groove is an open end while the other end is a sealed end, to facilitate the light more irradiating the teeth and gums of the patient. A positioning of the positioning slot may be located in a range of about 0.1 millimeter to about 10 millimeters from the opened end. Each groove of the dental cast includes an inner wall and an outer wall. In one embodiment, the positioning slot is preferably formed around the inner wall and in air communication with the groove, to facilitate the elimination of the pathogenic microbes located at the teeth and/or gums. In another embodiment, the positioning slot also can be formed around the outer wall and in air communication with the outside for the same purpose. A diameter of the positioning slot may be in a range of about 0.1 millimeter to about 1 millimeter. The diameter of the positioning slot may be preferably about 0.5 millimeter.

The positioning slot may be arranged on a position aligned with the gingiva or gums of the patient, to facilitate the effective elimination of the pathogenic microbes located at the teeth and/or gums. A predetermined distance from the positioning slot to a margin of the gingiva or gums adjacent to the dental crown may be in a range of about 0.1 millimeter to about 10 millimeters. The predetermined distance from the positioning slot to the margin of the gingiva or gums adjacent to the dental crown may be preferably in a range of about 0.5 millimeter to about 5 millimeters.

The LDF includes a core portion formed from silica glass. The core portion of the LDF includes a plurality of helical voids. The helical voids may be randomly distributed in the core portion and wrapped around a long axis of the LDF such that an angle between the long axis of the LDF and the plurality of helical voids is non-zero. A pitch of the helical voids may vary along the axial length of the LDF in order to achieve a desired illumination distribution along the lengthwise direction of the LDF. A cladding surrounds and is in direct contact with the core portion, wherein light guided by the core portion is scattered by the helical voids radially outward and through the cladding such that the LDF emits light with a predetermined intensity over an axial length of the LDF. A diameter of the LDF may be in a range of about 0.1 millimeter to about 1 millimeter. The diameter of the LDF may be preferably less than about 0.5 millimeter.

The light source instrument includes a light emitter. The light emitter may be selected from, but is not limited to, a laser diode, a light emitting diode, an ultraviolet emitter, a visible light emitter, an infrared light emitter, or other electroluminescent device. The light itself may be selected from, but is not limited to, an X-ray, an ultraviolet light, a visible light, or an infrared light. The infrared light is preferably an infrared laser ray. Thus, the light source instrument may provide the infrared laser ray to the dental device through the LDF for full oral cavity illumination.

The light is configured for treating the dental infection. The light is administered to the gums, the teeth, the tongue, and/or the soft tissue of lips of the patient. A wavelength of the light may be in a range of about 700 nanometers to about 900 nanometers. The wavelength of the light may be preferably in a range of about 750 nanometers to about 850 nanometers. The wavelength of the light may be more preferably in a range of about 800 nanometers to about 850 nanometers. In the embodiment, the preferred wavelength of the light may be 808 nanometers. A frequency of the light may be in a range of about 1 time per second to about 1000 times per second. The frequency of the light may be preferably in a range of about 1 time per second to about 500 times per second. The radiant intensity of the light may be less than about 10 Watts, preferably less than about 5 Watts, to facilitate the light passing through a certain depth of a tissue of the patient.

In block 103, the time period of irradiating the oral cavity is less than about 30 minutes. The time period of irradiating the oral cavity is preferably from about 60 seconds to about 30 minutes, with an ideal duration being from about 60 seconds to about 10 minutes. Furthermore, preferably irradiating the oral cavity for a period of less than about 30 minutes per square centimeter, or for a period of about 60 seconds to about 10 minutes per square centimeter of an area to be treated.

Figure 2:
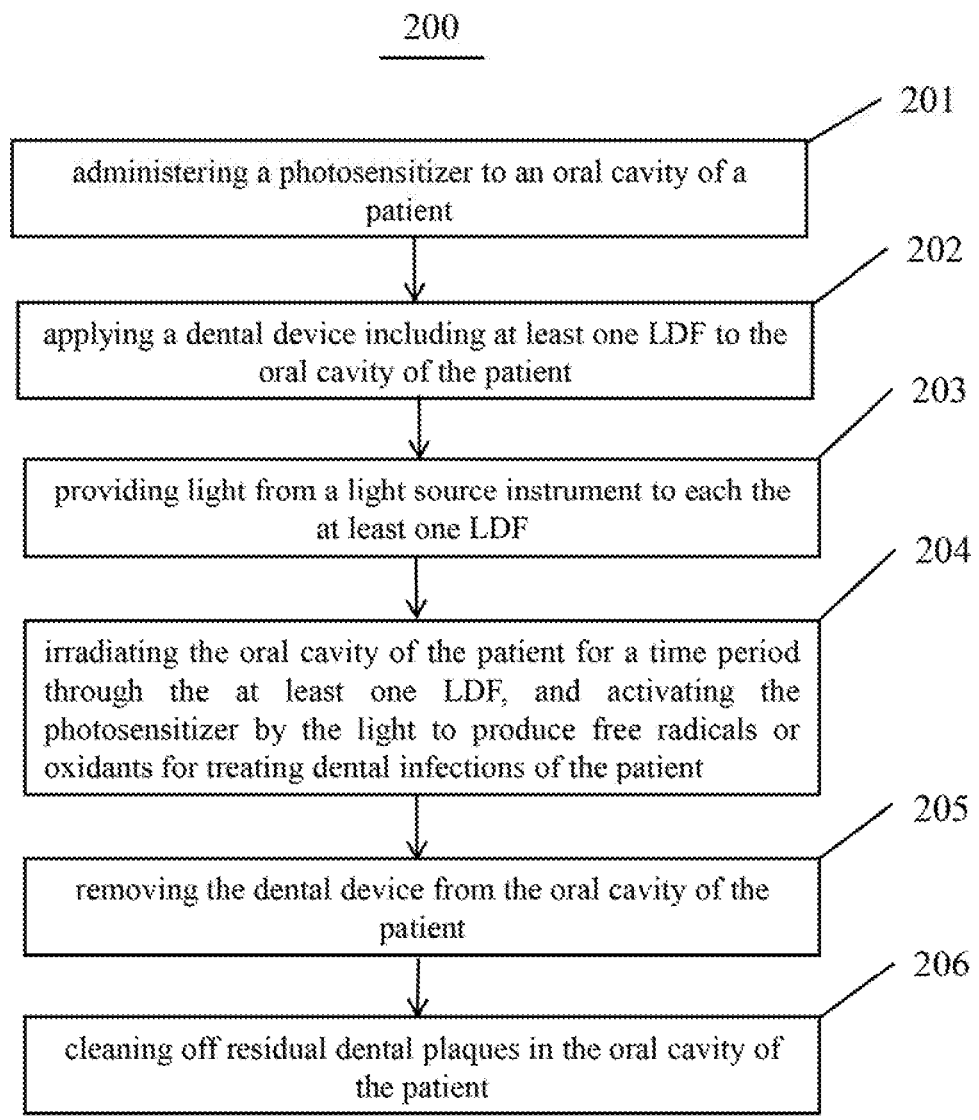
FIG. 2 is a block diagram of another exemplary embodiment of the photodynamic therapeutic method for treating dental infection.

As shown in FIG. 2, in the second embodiment, PDT method for treating dental infection includes the following steps:

in block 201, administering a photosensitizer to an oral cavity of a patient;
in block 202, applying a dental device including at least one LDF to the oral cavity of the patient;
in block 203, providing light from a light source instrument to each the at least one LDF;
in block 204, irradiating the oral cavity of the patient for a time period through the at least one LDF, and activating the photosensitizer by the light to produce free radicals or oxidants for treating dental infection of the patient;
in block 205, removing the dental device from the oral cavity of the patient; and
in block 206, cleaning off residual dental plaques in the oral cavity of the patient.

The above PDT method of the second embodiment is a substantially consistent with the steps of the first embodiment. The difference is that the PDT method of the second embodiment further includes the step of administering the photosensitizer to the oral cavity of the patient. That is, the photosensitizer may be administrated to the gums, the teeth, the tongue, and/or the soft tissue of lips of the patient. When the light with a certain wavelength irradiates towards the photosensitizer and reaches an excitation wavelength of the photosensitizer, the light may activate the photosensitizer to produce free radicals or oxidants. Thus, pathogenic microbes in the oral cavity of the patient will be killed. The required wavelength of the light may be the excitation wavelength of the photosensitizer which activates the photosensitizer or causes the photosensitizer to generate free radicals and oxidants for treating the dental infection.

The wavelength of the light may be more preferably in a range of about 800 nanometers to about 850 nanometers. The wavelength in a range of about 800 nanometers to about 850 nanometers may preferably activate the photosensitizer or preferably cause the photosensitizer to generate more free radicals and oxidants which destroy disease-causing bacteria and microbes. In the embodiment, the preferred wavelength of the light may be 808 nanometers, which is the preferable excitation wavelength of the photosensitizer.

The photosensitizer may be administered in a preferable amount to the oral cavity of the patient. The preferable amount of the photosensitizer may be in a range of about 0.1 nanomolar to about 10 millimolars. The preferable amount of the photosensitizer may be preferably in a range of about 0.1 micromolar to about 5 millimolars, to facilitate the photosensitizer generating enough free radicals and oxidants which destroy disease-causing bacteria and microbes. The amount of the photosensitizer may be proportional to a severity of dental infection of the patient.

The photosensitizer may be selected from, but is not limited to, at least one oxidant, at least one dye, or a combination thereof.

The at least one oxidant may be selected from the group consisting of hydrogen peroxide, carbamide peroxide, peroxy acid, alkali metal percarbonate benzoyl peroxide, or any combination thereof.

The at least one oxidant may be preferably selected from the group consisting of the hydrogen peroxide, the carbamide peroxide, or a combination thereof.

The at least one dye may be selected from the group consisting of pyronine Y, pyronine B, rhodamine B, rhodamine rhodamine WT, fluorescein, phloxine B, rose bengal, merbromine, eosin Y, eosin B, erythrosine B, methyl violet, neutral red, para red, amaranth, carrnoisine, allura red AC, tartrazine, orange G, ponceau 4R, methyl red, murexide-ammonium purpurate, saffranin O, basic fuchsin, acid fuschin, 3,3'-dihexylocarbocyanine iodide, carminic acid, indocyanine green (ICG), crocetin, α-crocin, a zeaxanthine, lycopene, α-carotene, β-carotene, bixin, fucoxanthine, or a combination thereof.

The ICG has low toxicity and fewer side effects. Furthermore, the US Food and Drug Administration has been officially approved the ICG for clinical use. Thus, the at least one dye is preferably the ICG.

The dosage form of the photosensitizer may be selected from the group consisting of a liquid form or a semi-solid form.

The liquid form of the photosensitizer may be selected from solution, suspension, emulsion, mucilage, or magmas. The solution is a homogeneous mixture comprised of two or more substances. The suspension is a heterogeneous mixture containing solid particles that are sufficiently large for sedimentation. The emulsion is a mixture of two or more different liquids that are normally immiscible. The mucilage is an aqueous solution usually as a viscid solution or a gum. The magma is often used to describe suspensions of inorganic solids, where there is a tendency for strong hydration and aggregation of the solid, giving rise to gel-like consistency and thixotropic rheological behavior.

The semi-solid form of the photosensitizer may be a cream, a gel, a paste, or a plaster. The cream is a semi-solid emulsion of oil and water. For example, water-in-oil (W/O) type cream is comprised of small droplets of water dispersed in a continuous oily phase. Oil-in-water (O/W) type cream is comprised of small droplets of oil dispersed in a continuous phase. The gel is a suspension of an insoluble drug in hydrated form wherein the particle size approaches or attains colloidal dimensions, and further contains a hydrogel and organogel types. The hydrogel type is a network of polymer chains that are hydrophilic. The hydrogel is highly absorbent natural or synthetic polymeric network. The organogel is a non-crystalline, non-glassy thermo-reversible (thermoplastic) solid material comprised of a liquid organic phase entrapped in a three-dimensionally cross-linked network. The paste consists of fatty base and at least 25% solid substance, and further includes aqueous cement and hydrophobic cement. The plaster is an adhesive substance that can be spread on fabric or other suitable backing material.

Figure 3:
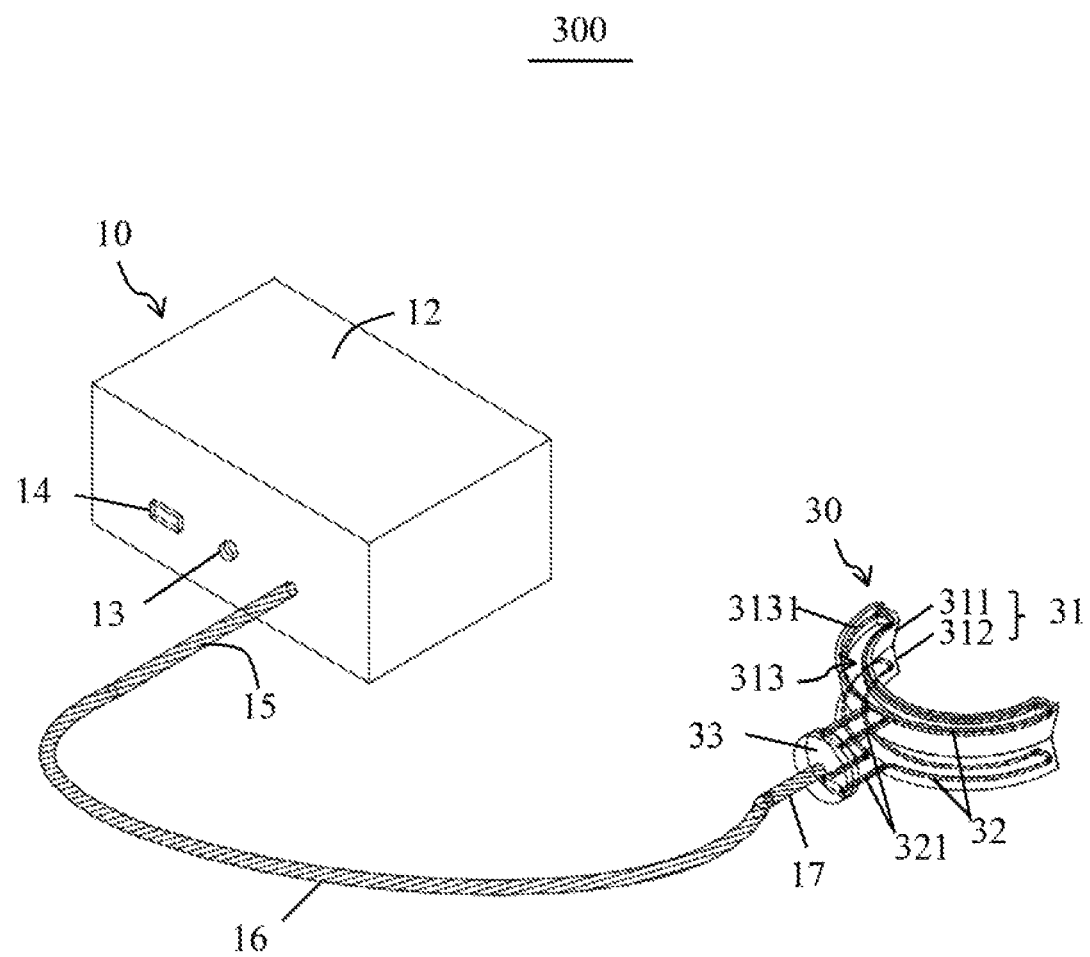
FIG. 3 is a schematic view of a photodynamic therapeutic system for treating dental infection in an embodiment of the disclosure.

As shown in FIG. 3, in the third embodiment, a photodynamic therapeutic system 300 for dental infection treatment includes a light source instrument 10 and a dental device 30 optically and detachably coupled to the light source instrument 10. The light source instrument 10 includes a main body 12, a switch 13, a power connection port 14, a first wire adaptor 15, a first LDF 16, and a second wire adaptor 17. The switch 13 controls the light source instrument to emit light. The power connection port 14 is electrically connected to an external power source or an inner battery. The power connection port 14 may be a universal serial bus (USB) port or a micro-USB port. The first LDF 16 has two ends. The first wire adaptor 15 and the second wire adaptor 17 are detachably coupled to opposite ends of the first LDF 16. One end of the first LDF 16 is optically connected to the main body 12 of the light source instrument 10 through the first wire adaptor 15. The other end of the first LDF 16 is optically connected to the dental device 30 through the second wire adaptor 17, to introduce the light from the light source instrument 10 into the dental device 30.

The light source instrument 10 may be a low power light source instrument. The light source instrument 10 further includes a light emitter. The light emitter may be selected from the group consisting of, but is not limited to, a laser diode, a light emitting diode, an ultraviolet emitter, a visible light emitter, an infrared light emitter, or other electroluminescent device.

The dental device 30 includes a dental cast 31 and at least one second LDF 32 and a connector 33. Each of the at least one second LDF 32 is arranged around the dental cast 31. Each of the at least one second LDF is optically coupled to the first LDF 16 of the light source instrument 10 through the connector 33.

In one embodiment, the dental cast 31 may include an upper alveolar 311 and a lower alveolar 312. The upper alveolar 311 and the lower alveolar 312 may be detachably fitted on the dental device 30. In the embodiment, the dental device 30 includes two second LDFs 32. Each of the at least one second LDF 32 includes a pair of third wire connectors 321 at the two ends. The third wire connectors 321 and the second wire adaptor 17 may be detachably coupled to the connector 33, and the third wire connectors 321 are optically coupled to the second wire adaptor 17 of the light source instrument 10 through the connector 33.

In another embodiment, the dental cast 31 may only include the upper alveolar 311 or the lower alveolar 312. The configuration of the upper alveolar 311 is substantially the same as that of the lower alveolar 312.

The upper alveolar 311 and the lower alveolar 312 are substantially symmetrical. Referring to FIG. 3, the upper alveolar 311 includes a groove 313 for accommodating the upper dental arch of the patient. An inner wall of the groove 313 includes a positioning slot 3131 formed in the inner wall for receiving the second LDF 32.

In one example, in use, the dental device 30 is applied to the oral cavity of the patient, and the upper dental arch/lower dental arch of the teeth sink into the groove of the dental cast 31. The power connection port 14 is connected to the external power source, and the switch 13 is pressed to supply electrical power to the light source instrument 10. The light emitted by the light source instrument 10 is transmitted from the first LDF 16 to the second LDF 32 of the dental cast 31. Thus, the light transmitted by the second LDFs 32 may irradiate the gums, the teeth, the tongue, and/or the muscle or soft tissue of lips of the patient, to facilitate killing of pathogenic microbes.

In another example, in use, the photosensitizer is administrated to the oral cavity of the patient before applying the dental device 30 to the oral cavity of the patient. Specifically, the photosensitizer may be administrated to the gums, the teeth, the tongue, and/or the muscle or soft tissue of lips of the patient. The light emitted by the light source instrument 10 is introduced into the oral cavity of the patient for a time period through the at least one LDF of the dental device 31 to activate the photosensitizer to produce free radicals or oxidants, and to facilitate the pathogenic microbes died.

Figure 4:
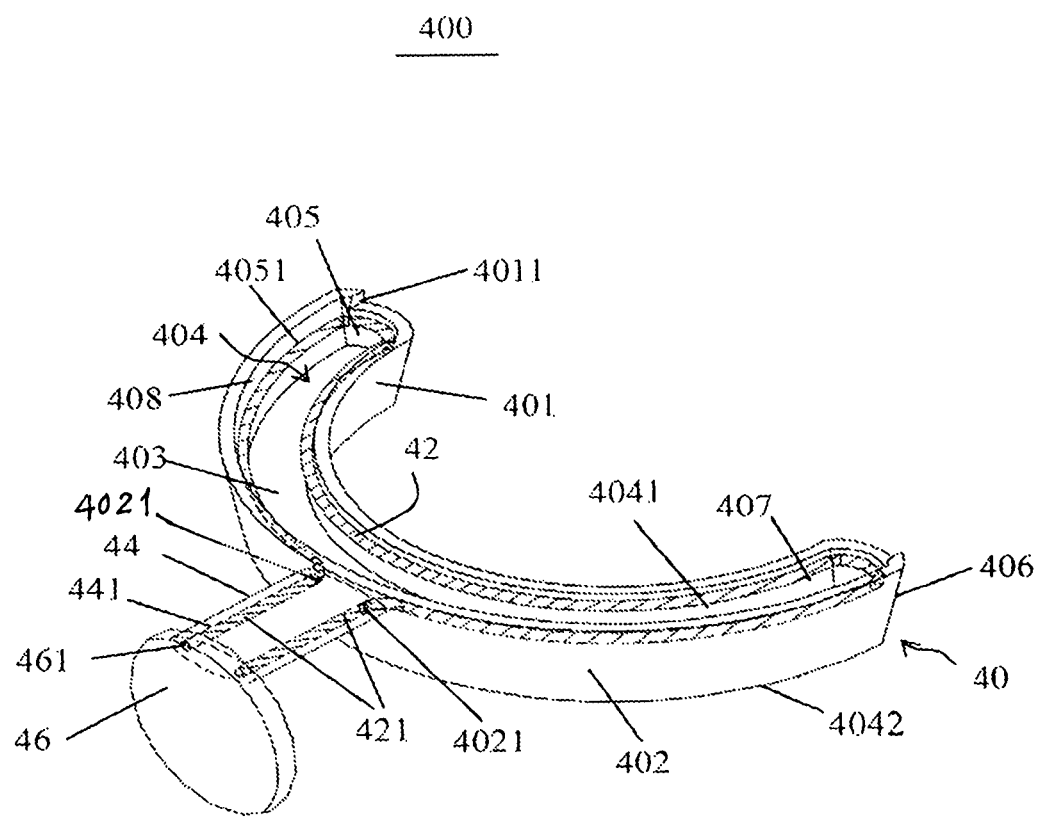
FIG. 4 is a perspective, enlarged view of a dental device with an upper alveolar for treating dental infection in an embodiment.

As shown in FIG. 4, in the fourth embodiment, a dental device 400 configured to be coupled to a light source instrument with a first LDF (not shown) includes a dental cast 40, a second LDF 42, and a connector 46. The dental device 400 is constructed from a dental brace. The dental cast 40, the second LDF 42, and the connector 46 may be detachably coupled to facilitate the replacement and/or the assembly of components. In the embodiment, the dental cast 40 includes an upper alveolar for receiving the upper dental arch of the patient. The second LDF 42 may be fitted on an upper end, a middle, or other position of the dental cast 40. In the embodiment, the second LDF 42 is preferably arranged on an upper end of the dental cast 40.

The dental cast 40 may further include a positioning member 44 arranged between the dental cast 40 and the connector 46. The positioning member 44 may be mounted on an upper end, a middle, or any suitable position of the connector 46. The positioning member 44 is preferably arranged on an upper end of the connector 46.

The dental device 400 may be based on a dental bite. An exterior of the dental cast 40 is substantially, but not limited to being, a U shape, a horse-shoe shape, or a slice. The shape of the dental cast 40 may be flexibly designed as a suitable size and/or shape, to accommodate the teeth and/or gums of the patient. The dental cast may be made any material that is biocompatible. For example, the material of the dental cast may be selected from the group consisting of a polymethylmethacrylate, polyethylene, polycarbonate, polyvinylchloride, polypropylene, polydimethyl siloxane, polytetrafluoroethylene, polyurethane, rubberized polymer, or any combination thereof. In the embodiment, the dental cast 40 is an upper alveolar. The upper alveolar may be any container shaped to accept teeth and/or gum of the patient. The upper alveolar may be at least partially made of a flexible material and also be at least partially made of a stiff material configured to support components of the dental device.

The dental cast 40 includes a front panel 401, a rear panel 402, and a bottom panel 403. The front panel 401, the rear panel 402, and the bottom panel 403 cooperatively form a groove 404 for receiving the teeth and/or gums of the patient. In the embodiment, the groove 404 is sealed, thus the molars of the upper dental arch of the patient may be completely sunk in the groove 404. In another embodiment, opposite ends of the groove 404 may be opened for better patient comfort. A thickness of the front panel 401, the rear panel 402, and the bottom panel 403 may be in a range of 0.1 millimeter to 10 millimeter, facilitating the comfortable use of the patient. The thickness of the front panel 401, the rear panel 402, and the bottom panel 403 may be preferably in a range of about 1 millimeter to about 5 millimeter. The front panel 401 may form a curve opening 4011 for closely and tightly accommodating the molars of the upper dental arch in the groove 404 of the dental cast 40, and facilitating the fixing of the dental cast 40 on the teeth and/or gums of the patient. A top end of a middle portion of the rear panel 402 defines two first positioning holes 4021 for the entry of the opposite ends of the second LDF 42. The bottom panel 403 may be a smooth surface to facilitate the bite between the upper dental arch and the lower dental arch of the patient.

A shape of the groove 404 is substantially semicircular. The groove 404 has an inner wall 405 and an outer wall 406. In the embodiment, the groove 404 around the inner wall 405 forms a positioning slot 4051 in air communication with the groove 404. The positioning slot 4051 is configured for receiving the second LDF 42. In another embodiment, the groove 404 around the outer wall 406 may also form the positioning slot 4051 in air communication with the outside and configured for receiving the second LDF 42. The second LDF 42 is detachably received and mounted in the positioning slot 4051. The inner wall 405 includes a coronal contact surface 407 and a gum contact surface 408. The positioning slot 4051 may be preferably arranged between the coronal contact surface 407 and a gum contact surface 408.

The groove 404 has two ends. One end of the groove 404 is an open end 4041 while the other end is a sealed end 4042, to facilitate the light more irradiating the teeth and gums of the patient. A positioning of the positioning slot 4051 may be located in a range of about 0.1 millimeter to about 0.5 millimeters from the opened end 4041.

When the teeth and/or gums of the upper dental arch are enclosed in the dental cast 40, the front panel 401 is located between an inner side of the upper dental arch and the tongue. The rear panel 402 is located between an outside of the upper dental arch and the upper lip, and the bottom panel 403 is attached to or abutted against the lower dental arch. Furthermore, the dental coronal is attached to or abutted against the coronal contact surface 407, and the gums are attached to or abutted against the gum contact surface 408. Thereby, the light transmitted by the second LDF 42 may irradiate the gums, the teeth, the tongue, and/or the muscle or soft tissue of lips of the patient. The light may thus activate the photosensitizer within the oral cavity to produce free radical or oxidant, facilitating the pathogenic microbes died.

The positioning slot 4051 is situated in the dental cast for the LDF setting. A diameter of the positioning slot 4051 may be substantially in a range of 0.1 millimeter to 1 millimeter. The diameter of the positioning slot 4051 may be preferably about 0.5 millimeter. The diameter of the positioning slot is substantially consistent with the LDF and its diameter, facilitating the embedding of the second LDF 42 in the positioning slot 4051. A predetermined distance from the positioning slot 4051 to a margin of the dental crown may be in a range of about 0.1 millimeter to about 10 millimeter; the predetermined distance from the positioning slot 4051 to the margin of the dental crown may be preferably in a range of about 0.5 millimeter to about 5 millimeter. A predetermined distance from the positioning slot 4051 to a margin of the gum may be in a range of about 0.1 millimeter to about 10 millimeter. The predetermined distance from the positioning slot 4051 to the margin of the gum may be preferably in a range of about 0.5 millimeter to about 5 millimeter.

The second LDF 42 may include a pair of first wire connectors 421 at ends thereof. Each of the first wire connectors 421 has two ends. One end of the first wire connector 421 is optically connected to the connector 46, and the other end of the first wire connector 421 is coupled to the opposite ends of the second LDF 42. The pair of the first wire connectors 421 may be detachably coupled to the second LDF 42 or integrally formed with the second LDF 42. In the embodiment, the pair of the first wire connectors 421 is detachably coupled to the second LDF 42. A diameter of the second LDF 42 is preferably and substantially 0.5 millimeter.

The positioning member 44 defines two second positioning holes 441 along an axial direction of the positioning member 44, and the second positioning holes 441 align with the first positioning holes 4021 of the rear panel 402. The pair of first wire connectors 421 may be arranged in parallel with the second positioning holes 441 of the positioning member 44.

The connector 46 may include a plurality of adapters 461 optically connected to the first wire connectors 421 of the second LDF 42. In the embodiment, the first LDF (not shown) of the light source instrument is optically coupled to the first wire connectors 421 of the second LDF 42 via the adapters 461 of the connector 46.

In another embodiment, the dental device 400 may also include a second wire connector (not shown) optically coupled to the first LDF (not shown) of the light source instrument (not shown). The second wire connector (not shown) is arranged on one end of the connector 46 opposite to the dental cast 40. The second wire connector (not shown) may be optically connected to the connector 46.

Figure 5:
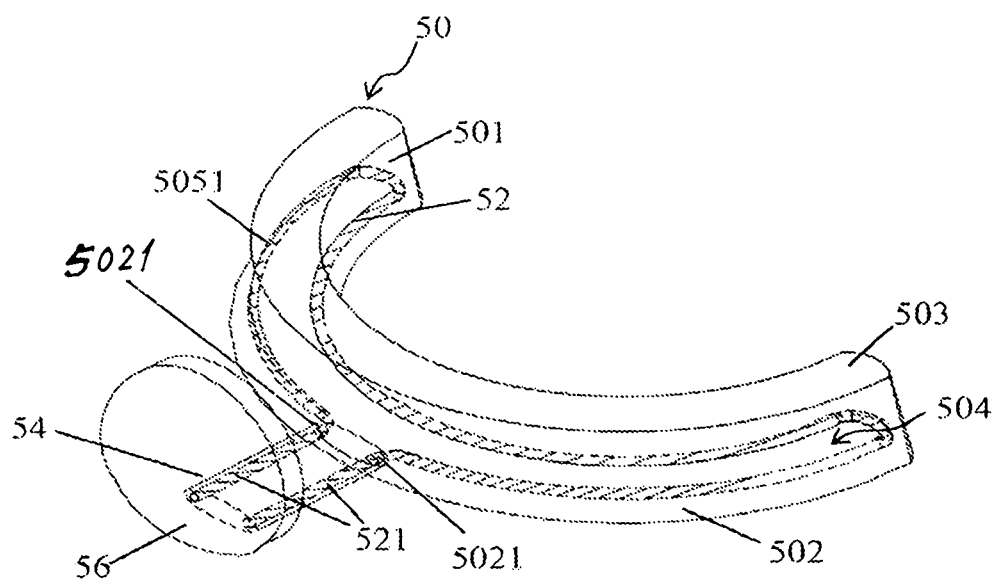
FIG. 5 is a perspective, enlarged view of the dental device with a lower alveolar for treating dental infection in another embodiment.

As shown in FIG. 5, in the fifth embodiment, a dental device 500 is coupled to a light source instrument with a first LDF (not shown). The dental device 500 constructed with a dental brace includes a dental cast 50, a second LDF 52, a positioning member 54, and a connector 56. The dental cast 50, the second LDF 52, the positioning member 54, and the connector 56 are substantially consistent features among the structures of the fourth embodiment. The difference is that the dental cast 50 is a lower alveolar for receiving the lower dental arch of the patient.

The dental cast 50 includes a front panel 501, a rear panel 502, and a top panel 503. The front panel 501, the rear panel 502, and the top panel 503 cooperatively form a groove 504 for receiving the teeth and/or gums. The top panel 503 may be a smooth surface to facilitate the bite between the upper dental arch and the lower dental arch of the patient. The groove 504 has two ends. One end of the groove 504 is an open end (not shown) while the other end is a sealed end (not shown), to facilitate the light more irradiating the teeth and gums of the patient. A positioning of the groove 504 may be located in a range of about 0.1 millimeter to about 10 millimeters from the opened end (not shown).

The groove 504 has an inner wall. The groove 504 around the inner wall forms a positioning slot 5051 communicating with the groove 504. The second LDF 52 is detachably received and mounted in the positioning slot 5051. A bottom end of a middle portion of the rear panel 502 defines two first positioning holes 5021 for entry of opposite ends of the second LDF 52. In the embodiment, the second LDF 52 and the positioning member 54 are preferably arranged on a lower end of the dental cast 50, and the positioning member 54 is preferably arranged on a lower end of the connector 56. When the lower dental arch of the teeth is in the dental cast 50, the front panel 501 is located between an inner side of the lower dental arch and the tongue. The rear panel 502 is located between an outside of the lower dental arch and the lower lip, and the bottom panel 503 is attached to or abutted against the upper dental arch. The light transmitted by the second LDF 52 may irradiate the gums, the teeth, the tongue, and/or the soft tissue of lips of the patient. Thus, the light may activate the photosensitizer within the oral cavity to produce free radical or oxidant, facilitating the pathogenic microbes died.

Figure 6:
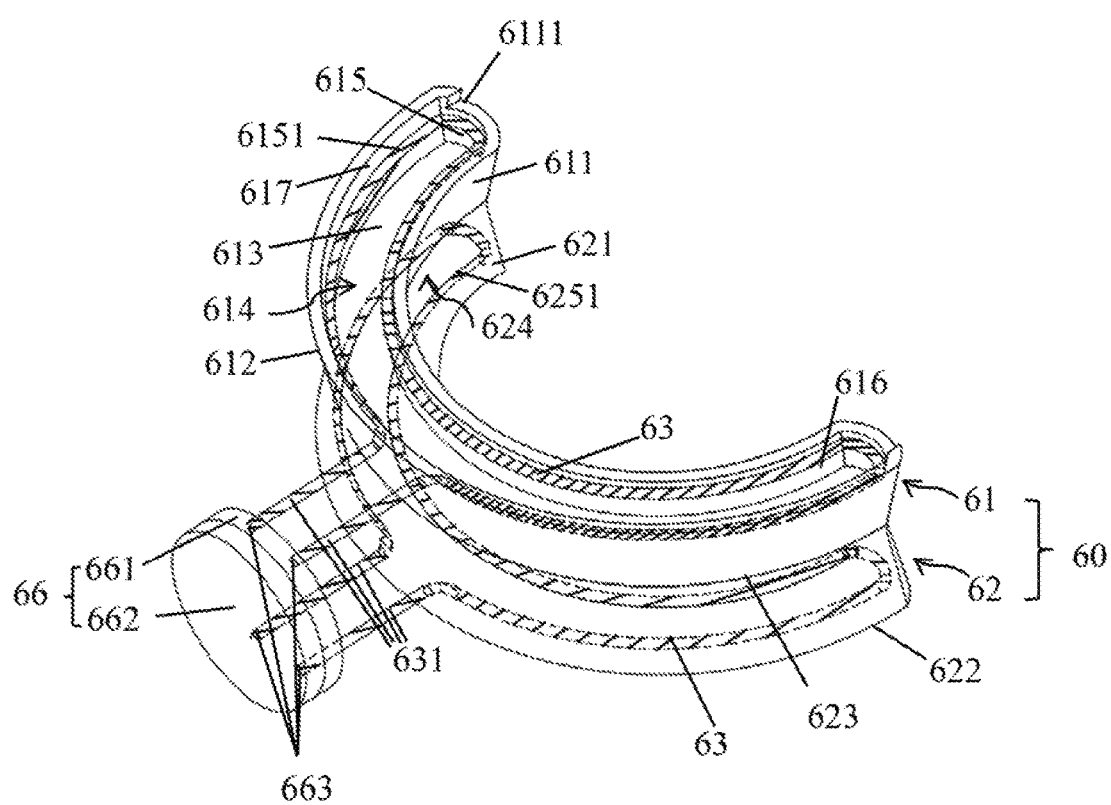
FIG. 6 is a perspective, enlarged view of the dental device having an upper alveolar and a lower alveolar for treating dental infection in another embodiment.

As shown in FIG. 6, in the sixth embodiment, a dental device 600 is coupled to a light source instrument with a first LDF (not shown). The dental device 600 constructed with a dental brace includes a dental cast 60, a pair of second LDFs 63, and a connector 66. The dental cast 60, the second LDFs 63, the positioning member 64, and the connector 66 are substantially consistent features among the structures of the fourth embodiment and the fifth embodiment. The difference is that the connector 66 includes a first connecting portion 661 and a second connecting portion 662. The dental cast 60 includes an upper alveolar 61 for receiving the upper dental arch of the patient, and a lower alveolar 62 for receiving the lower dental arch of the patient.

The second LDFs 63 of the dental device 600 are optically coupled to the first LDF (not shown) of the light source instrument through the first connecting portion 661 and the second connecting portion 662. One side of the first connecting portion 661 adjacent to the dental cast 60 may include a plurality of adapters 663 optically connected to opposite ends of each second LDF 63. The second connecting portion 662 is optically connected to the first LDF (not shown), and the first connecting portion 661 is optically coupled to the second connecting portion 662.

The upper alveolar 61 and the lower alveolar 62 are substantial symmetrical. The upper alveolar 61 and the lower alveolar 62 are substantially consistent features among the structures of the fourth embodiment and the fifth embodiment.

Figure 7:
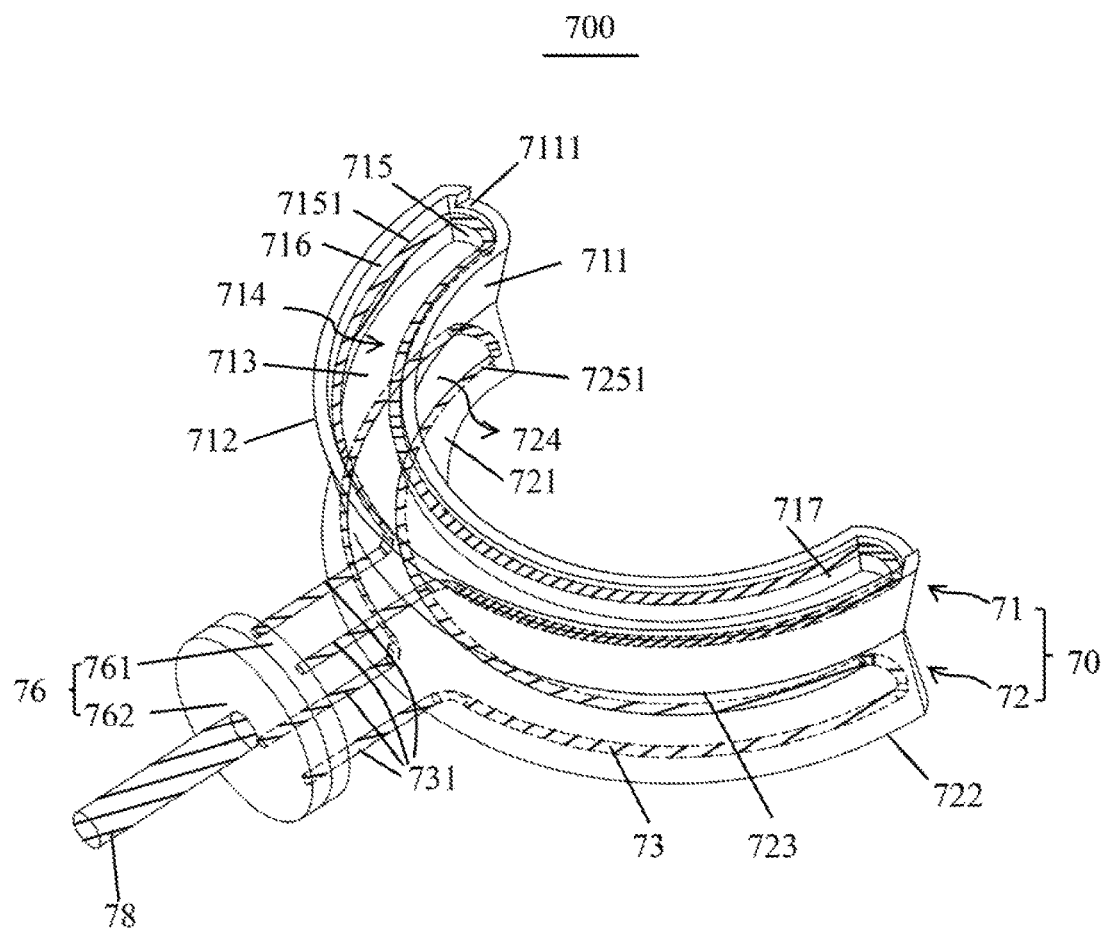
FIG. 7 is a perspective, enlarged view of a dental brace with a wire connector for treating dental infection in an embodiment.

As shown in FIG. 7, in the seventh embodiment, a dental device 700 is optically coupled to a light source instrument with a first LDF (not shown). The dental device 700 constructed with a dental brace includes a dental cast 70, a pair of second LDFs 73, and a connector 76. The dental cast 70, the second LDFs 73, and the connector 76 are substantially consistent features among the structures of the sixth embodiment. The difference is that the dental device 700 further includes a wire connector 78 detachably coupled to the connector 76 and arranged on one side of the connector 76 opposite to the dental cast 70.

The first LDF (not shown) and the second LDFs 73 of the dental device 700 can be optically coupled through the wire connector 78.

Figure 8:
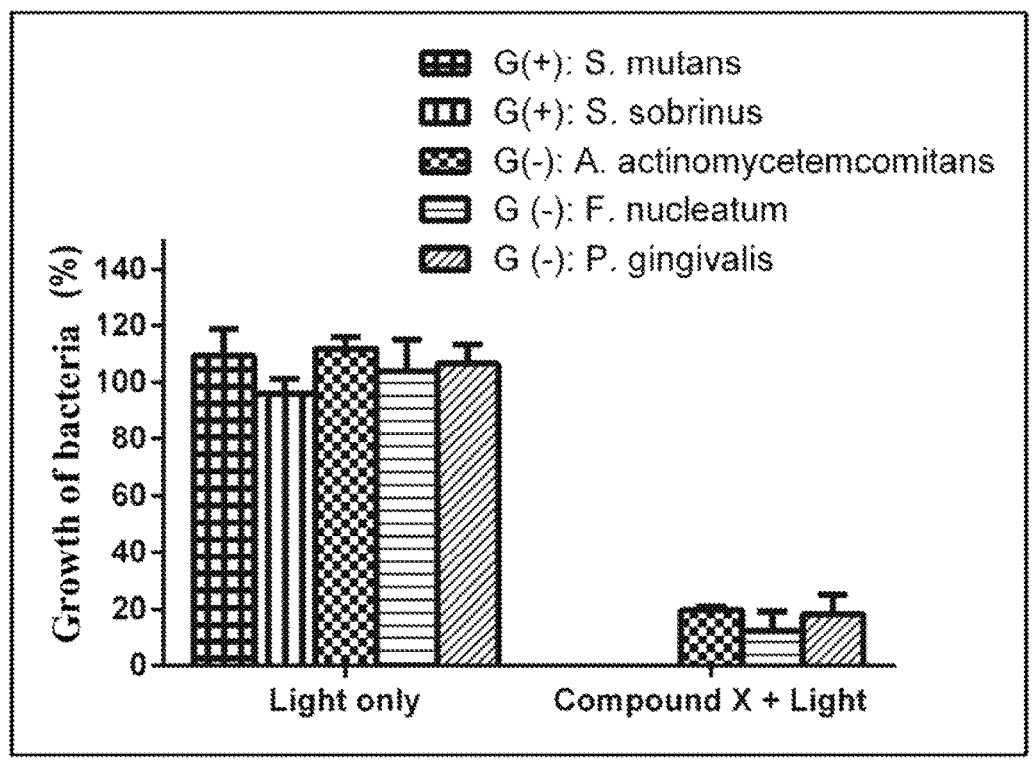
FIG. 8 graphically depicts the assay results of bacterial disinfection by using the PDT method of treating dental infection, applying a specific photosensitizer and a specific illuminating wavelength.

FIG. 8 shows the assay results of different bacterial disinfection using the photodynamic therapy method in vitro with a specific compound X and/or a specific light. In particular, FIG. 8 shows two group assays. One group assay represents the different bacterial disinfection by using the photodynamic therapy method in vitro with a specific irradiated wavelength of the light, and the other group assay represents the different bacterial disinfection by using the photodynamic therapy method in vitro with a specific compound X and the specific irradiated wavelength of the light. FIG. 8 shows a growth rate of the bacteria under different assay conditions using the photodynamic therapy method.

The light is infrared laser ray. The specific irradiated wavelength of the infrared laser ray of is 808 nanometers. The specific compound X is a photosensitizer. The photosensitizer is the indocyanine green dye. The period of irradiating the bacteria is about 5 minutes. The bacteria include gram positive (G (+)) bacteria and gram negative (G (−)) bacteria. The G (+) bacteria include a *Streptococcus mutans* (*S. mutans*) and a *Streptococcus sobrinus* (*S. sobrinus*). The G (−) bacteria include an *Aggregatibacter actinomycetemcomitans* (*A. actinomycetemcomitans*), a *Fusobacterium nucleatum* (*F. nucleatum*), and a *Porphyromonas gingivalis* (*P. gingivalis*).

Referring to FIG. 8, when the photodynamic therapy method in vitro uses the specific photosensitizer and the specific irradiated wavelength of the light, the G (+) bacterial show the percentage growth rate as zero, and the G (−) bacteria show the percentage growth rate as less than 20%.

When the photodynamic therapy method in vitro only uses the specific irradiated wavelength of the light, the G (+) bacteria and the G (−) bacteria have the percentage growth rate of between 80% and 120%.

In contrast to the photodynamic therapy method with the specific irradiated wavelength of the light, the photodynamic therapy method with the specific irradiated wavelength of the light and the specific photosensitizer is better for treating dental infection of the patient because the photodynamic therapy method with the specific irradiated wavelength of the light and the specific photosensitizer show lower growth rates of the bacteria.

The embodiments illustrated and described above are only examples. Many details are often found in the art such as the other features of a dental device and a photodynamic therapeutic system. Therefore, many such details are neither illustrated nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A dental device for treating dental infection of a patient, comprising:
    a dental cast comprising at least one groove for receiving teeth and/or gums of a dental arch of the patient;
    at least one light diffusing fiber arranged on the dental cast around the at least one groove, wherein the at least one light diffusing fiber is configured to convey light treating dental infection of the patient; and
    a connector and a positioning member arranged between the connector and the dental cast, wherein the connector is optically coupled to the at least one light diffusing fiber; wherein the at least one light diffusing fiber comprises a pair of first wire connectors at two ends thereof, wherein the connector comprises a plurality of adapters optically coupled to one end of the first wire connectors, and the other end of the first wire connectors is correspondingly coupled to the two opposite ends of the at least one light diffusing fiber.

2. The dental device of claim 1, wherein each of the at least one groove of the dental cast comprises an inner wall, and wherein the dental cast further comprises a positioning slot formed in the inner wall, the positioning slot is in air communication with each of the at least one groove and configured for receiving the at least one light diffusing fiber.

3. The dental device of claim 2, wherein a diameter of the positioning slot is substantially consistent with a diameter of the at least one light diffusing fiber.

4. The dental device of claim 3, wherein the diameter of the at least one light diffusing fiber is in a range of about 0.1 millimeter to about 1 millimeter and the diameter of the positioning slot is in a range of about 0.1 millimeter to about 1 millimeter.

5. The dental device of claim 1, wherein the dental cast comprises an upper alveolar, a lower alveolar, or a combination thereof, and the upper alveolar is adapted for receiving an upper dental arch of the dental arch in said upper alveolar and the lower alveolar is adapted for receiving a lower dental arch of the dental arch in said lower alveolar.

6. The dental device of claim 1, wherein the first wire connectors are detachably coupled to the at least one light diffusing fiber or integrally formed with the at least one light diffusing fiber.

7. The dental device of claim 1, further comprising a second wire connector detachably coupled to the connector and arranged on one side of the connector opposite to the dental cast.

8. The dental device of claim 1, wherein the dental cast comprises a front panel, a rear panel, and a bottom panel; the front panel, the rear panel, and the bottom panel cooperatively form the at least one groove.

9. The dental device of claim 1, wherein the at least one groove includes an open end, and a sealed end opposite to said open end, and wherein a positioning of a positioning slot is located in a range of about 0.1 millimeter to about 10 millimeters from the open end.

10. The dental device of claim 1, wherein the front panel comprises a curve opening, the curve opening is configured for accommodating two opposite molars of the upper dental arch; and wherein a middle portion of the rear panel comprises two first positioning holes for respectively penetrating two ends of the light diffusing fiber into said two first positioning holes.

11. A photodynamic therapeutic system for treating dental infection of a patient, comprising:
    a dental device, comprising:
        a dental cast comprising at least one groove for receiving teeth and/or gums of a dental arch of the patient, wherein the at least one groove includes an open end, and a sealed end opposite to said open end, and wherein a positioning of a positioning slot is located in a range of about 0.1 millimeter to about 10 millimeters from the open end; and
        at least one first light diffusing fiber arranged on the dental cast around the at least one groove;
    a light source instrument emitting light; and
    a photosensitizer adapted to be spread or sprayed to an oral cavity of the patient,
    wherein the dental device is optically coupled to the light source instrument, the light is transmitted by the at least one first light diffusing fiber of the dental device to the oral cavity of the patient, and wherein the photosensitizer is activated by the light to produce free radicals or oxidants for treating dental infection of the patient.

12. The dental device of claim 11, wherein each of the at least one groove of the dental cast comprises an inner wall, and wherein the positioning slot is formed in the inner wall, and the positioning slot is in air communication with each of the at least one groove and configured for receiving the at least one first light diffusing fiber.

13. The dental device of claim 11, wherein a diameter of the positioning slot is substantially consistent with a diameter of the first light diffusing fiber.

14. The dental device of claim 13, wherein the diameter of the at least one first light diffusing fiber is in a range of about 0.1 millimeter to about 1 millimeter and the diameter of the positioning slot is in a range of about 0.1 millimeter to about 1 millimeter.

15. The photodynamic therapeutic system of claim 11, wherein a spread or sprayed amount of the photosensitizer is in a range of about 0.5 nanomolar to about 5 millimolars.

16. The photodynamic therapeutic system of claim 11, wherein the photosensitizer is selected from at least one oxidant, at least one dye, or a combination thereof.

17. The photodynamic therapeutic system of claim 11, wherein the light source instrument comprises a light emitter, wherein the light emitter comprises a laser diode, a light emitting diode, an ultraviolet emitter, a visible light emitter, infrared light emitter, or other electroluminescent devices.

18. The photodynamic therapeutic system of claim 11, wherein the light comprises an X-ray, an ultraviolet light, a visible light, or an infrared light, wherein the infrared light is infrared laser ray.

19. The photodynamic therapeutic system of claim 11, wherein a radiant intensity of the light is less than about 10 Watts.

20. The photodynamic therapeutic system of claim 11, wherein a wavelength of the light is in a range of about 700 nanometers to about 900 nanometers.

21. The photodynamic therapeutic system of claim 11, wherein the light source instrument comprises a second light diffusing fiber optically coupled to the at least one first light diffusing fiber of the dental device.

* * * * *